(12) United States Patent
Zhang

(10) Patent No.: US 11,844,744 B1
(45) Date of Patent: Dec. 19, 2023

(54) MICROWAVE PHYSIOTHERAPY ACUPOINT ACUPUNCTURE DEVICE AND USE METHOD THEREOF

(71) Applicant: Henan Lixinghe Medical Technology Co., Ltd., Henan (CN)

(72) Inventor: Yanming Zhang, Henan (CN)

(73) Assignee: HENAN LIXINGHE MEDICAL TECHNOLOGY CO., LTD, Kaifeng (CN)

( * ) Notice: Subject to any disclaimer, the term of this patent is extended or adjusted under 35 U.S.C. 154(b) by 0 days.

(21) Appl. No.: 18/200,271

(22) Filed: May 22, 2023

(30) Foreign Application Priority Data

Sep. 7, 2022 (CN) ......................... 202211087235.X

(51) Int. Cl.
*A61H 39/04* (2006.01)
*A61H 39/00* (2006.01)

(52) U.S. Cl.
CPC ....... *A61H 39/04* (2013.01); *A61H 2039/005* (2013.01); *A61H 2201/5025* (2013.01)

(58) Field of Classification Search
CPC ........ A61H 39/00; A61H 39/04; A61H 39/08; A61H 2039/005; A61H 2201/0142; A61H 2201/5025; A61N 5/02; A61N 5/022; A61N 5/025; A61N 5/04; A61N 5/045; A61N 2005/027

See application file for complete search history.

(56) References Cited

FOREIGN PATENT DOCUMENTS

| CN | 215275441 | * 12/2021 | ............. A61H 36/06 |
| WO | WO-2021217675 A1 | * 11/2021 | ............. A61H 39/04 |

* cited by examiner

*Primary Examiner* — Robert A Lynch
(74) *Attorney, Agent, or Firm* — Kirk A. Wilson; Joseph T. Guy; Patent Filing Specialist Inc.

(57) ABSTRACT

Disclosed is a microwave physiotherapy acupoint acupuncture device, including a main console, and a physiotherapy couch. An end part of the physiotherapy couch is provided with a mounting frame and a control box, the mounting frame is provided with a patient parameter display screen, a microwave source is arranged in a control box, and a control panel is provided outside the control box. A side part of the physiotherapy couch is provided with a mounting box, a microwave magnetron is arranged inside the mounting box, and a mechanical arm is arranged at a top of the mounting box. An end part the mechanical arm is provided with a microwave probe, and the microwave magnetron is connected to the microwave probe at the end part of the mechanical arm by a line.

8 Claims, 2 Drawing Sheets

MICROWAVE PHYSIOTHERAPY ACUPOINT ACUPUNCTURE DEVICE AND USE METHOD THEREOF

CROSS-REFERENCE TO RELATED APPLICATION

This patent application claims priority of International Patent Application No. PCT/CN2023/071836, filed on Jan. 12, 2023, which claims the priority of Chinese Patent Application No. 202211087235.X filed with the China National Intellectual Property Administration on Sep. 07, 2022, and entitled "Microwave physiotherapy acupoint acupuncture device and use method thereof", the disclosure of which is incorporated herein in its entirety by reference.

TECHNICAL FIELD

The present disclosure belongs to the technical field of microwave acupoint acupuncture devices, and in particular to a microwave physiotherapy acupoint acupuncture device and a use method thereof.

BACKGROUND

Microwave refers to an electromagnetic wave with a frequency from 300 MHz to 300 GHz, which is the abbreviation of a limited frequency band in radio waves, i.e., the electromagnetic wave with a wavelength from 1 mm to 1 meter. Microwave frequency is higher than that of ordinary radio waves, which is also commonly called "ultra-high frequency electromagnetic wave". As the electromagnetic wave, microwave also has wave-particle duality. The basic properties of the microwave usually show three characteristics: penetration, reflection and absorption.

Microwave acupuncture is a method of treating diseases by connecting a microwave antenna to a needle handle and injecting microwaves into acupoints or directly irradiating the acupoints based on filiform needle acupuncture. It is a new acupuncture therapy combining modern microwave technologies with traditional acupuncture methods.

At present, existing microwave physiotherapy acupoint acupuncture instruments in the market are single instruments with a single probe, and the single probe needs to be held by a worker for an acupuncture operation. When multiple acupoints of a patient are required to be acupunctured at the same time, the existing microwave physiotherapy acupoint acupuncture instruments cannot meet the requirements.

SUMMARY

A microwave physiotherapy acupoint acupuncture device and a use method thereof are provided. Compared with the existing microwave acupuncture equipment, an integrated microwave physiotherapy acupoint acupuncture device structure is employed, when a patient lies on a physiotherapy couch, ten acupoints of the patient can be subjected to microwave physiotherapy at the same time, and a lying posture of the patient can be adjusted through an electric physiotherapy couch, thus further improving the effect of microwave physiotherapy.

The technical solution adopted by the present disclosure for solving the technical problems is as follows:

A microwave physiotherapy acupoint acupuncture device includes a main console, and a physiotherapy couch. An end part of the physiotherapy couch is provided with a mounting frame and a control box. The mounting frame is provided with a patient parameter display screen, a microwave source is arranged inside the control box, and a control panel is arranged outside the control box. A side part of the physiotherapy couch is provided with a mounting box, a microwave magnetron is arranged inside the mounting box, and a mechanical arm is arranged at a top of the mounting box. An end part of the mechanical arm is provided with a microwave probe, and the microwave magnetron is connected to the microwave probe at the end part of the mechanical arm through a line. The main console is respectively connected to the display screen, the microwave source, the control panel, the microwave magnetron, and the microwave probe through lines. The control panel is respectively connected to the display screen, the microwave source, the microwave magnetron, and the microwave probe through lines.

At least ten microwave magnetrons are arranged inside the mounting box, and at least ten mechanical arms are arranged at the top of the mounting box. Each microwave magnetron is correspondingly connected to the microwave probe on one of mechanical arms through a line.

The mechanical arm is a three-joint mechanical arm, or a universal bamboo pipe.

The mounting frame is of n circular arc structure, and a metal detector is arranged on a lower side face of a top of the mounting frame.

The physiotherapy couch is an electric physiotherapy couch.

A use method of a microwave physiotherapy acupoint acupuncture device includes the following steps:

(a) turning on a power supply and electrifying the whole acupoint acupuncture device, thus making the microwave physiotherapy acupoint acupuncture device in a standby state at the moment;

(b) settling a patient on a physiotherapy couch 2, confirming that no metal is on and in the body of the patient, confirming acupoints to be subjected to physiotherapy, and adjusting positions of mechanical arms to align with the acupoints;

(c) setting duration of physiotherapy, where the duration of physiotherapy is 0 to 30 minutes for a single session, preferably 15 minutes for a single session and three sessions for a course of treatment;

(d) turning on microwave sources one by one through a main console or a control panel, adjusting output power to an acceptable range of the body of the patient, paying close attention to reaction of the patient during physiotherapy, communicating with the patient for body feeling in time, and pressing a stop button immediately to cut off the microwave output instantly in case of an emergency;

(e) if the patient has no adverse reaction, sending, by the control panel, a prompt tone five seconds before the end of physiotherapy, then stopping microwave output, and printing, by the main console, physiotherapy parameters; and (f) removing the mechanical arms from the body of the patient, slowly settling the patient in a rest area to rest for 10 minutes, where after the observation period, the patient is free to move if no abnormal reaction exists.

A microwave connection port is checked and screwed before physiotherapy, and a microwave probe interface is checked again after physiotherapy, so as to ensure the firmness and reliability of the interface.

The microwave probes cannot be directly opposed to each other.

The present disclosure has the beneficial effects that:

By adopting the above technical solution, the present disclosure has the beneficial effects that:

Compared with the existing microwave acupuncture equipment, an integrated microwave physiotherapy acupoint acupuncture device structure is employed, when a patient lies on a physiotherapy couch, ten acupoints of the patient can be subjected to microwave physiotherapy at the same time, and a lying posture of the patient can be adjusted through an electric physiotherapy couch, thus further improving the effect of microwave physiotherapy. Ten existing microwave acupuncture devices are required to achieve the use effect of the acupoint acupuncture device of the present disclosure. Microwave treatment of diseases is mainly achieved through thermal and biological effects. When acting on body tissues, the microwave may cause high-frequency oscillation of ions, water molecules and dipoles in tissue cells. When the microwave is low in output energy and less in radiant heat energy, local blood circulation can be increased, local metabolism can be accelerated, and local immunity can be enhanced. Therefore, the device can effectively improve local blood circulation, promote edema absorption, diminish inflammation, and relieve pain.

In conclusion, a microwave physiotherapy acupoint acupuncture device and a use method thereof are provided. Compared with the existing microwave acupuncture equipment, an integrated microwave physiotherapy acupoint acupuncture device structure is employed, when a patient lies on a physiotherapy couch, ten acupoints of the patient can be subjected to microwave physiotherapy at the same time, and a lying posture of the patient can be adjusted through an electric physiotherapy couch, thus further improving the effect of microwave physiotherapy.

DETAILED DESCRIPTION OF THE EMBODIMENTS

In the present disclosure, unless expressly specified and limited otherwise, it also should be noted that the terms "arrange", "mount", "connected", "connection" and the like should be understood broadly, e.g., may be either a fixed connection or a detachable connection, or a connection in one piece; may be a mechanical connection or an electrical connection; may be a direct connection or an indirect connection through an intermediate medium, or may be an internal communication between two elements. For those of ordinary skill in the art, the specific meanings of the above terms in the present disclosure can be understood on a case-by-case basis.

The following clearly and completely describes the technical solutions in the embodiments of the present disclosure with reference to the accompanying drawings in the embodiments of the present disclosure. Apparently, the described embodiments are merely a part rather than all of the embodiments of the present disclosure. All other embodiments obtained by those of ordinary skill in the art based on the embodiments of the present disclosure without creative efforts shall fall within the protection scope of the present disclosure.

Figure 1:
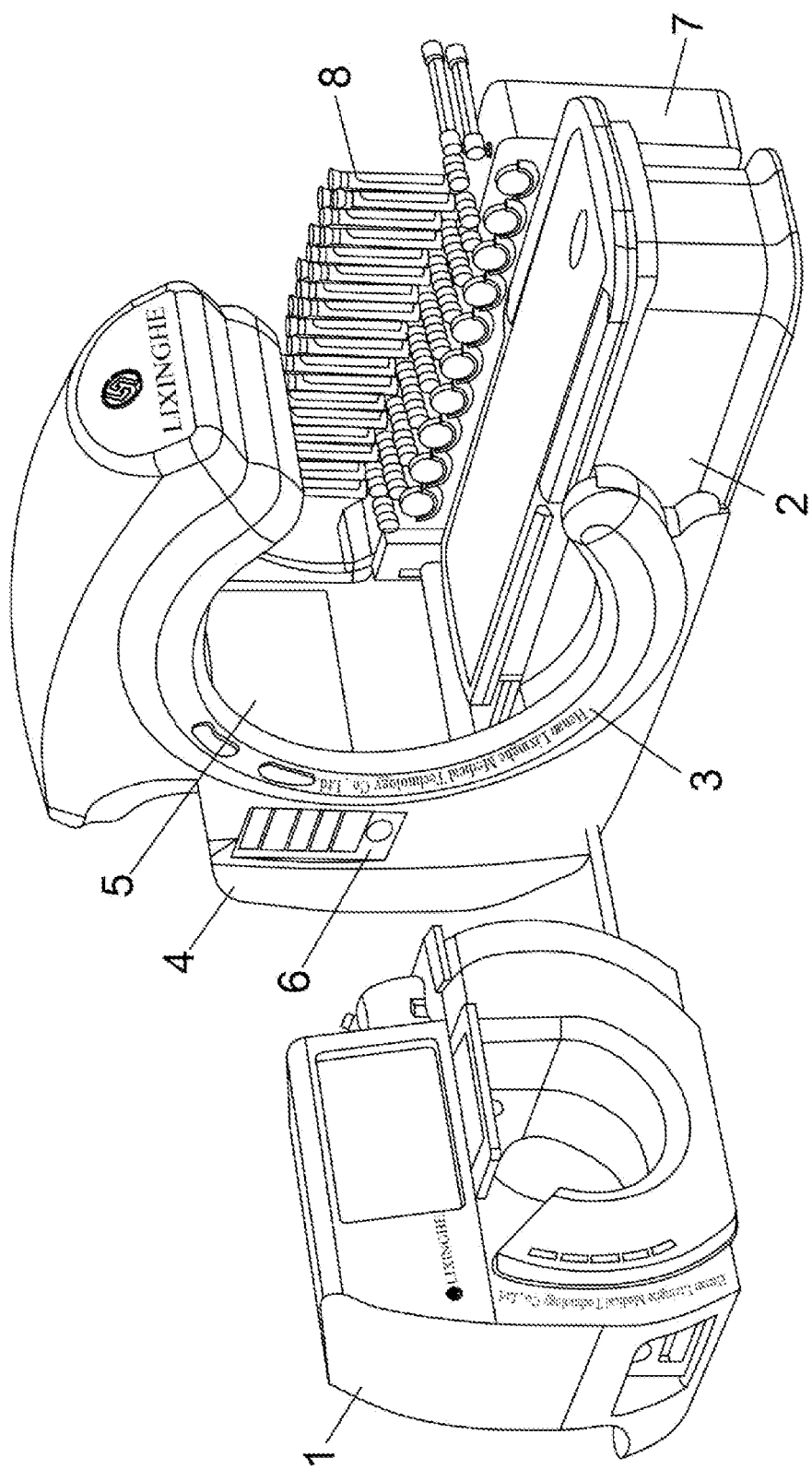
FIG. 1 is a first schematic diagram of a structure in accordance with the present disclosure.
Figure 2:
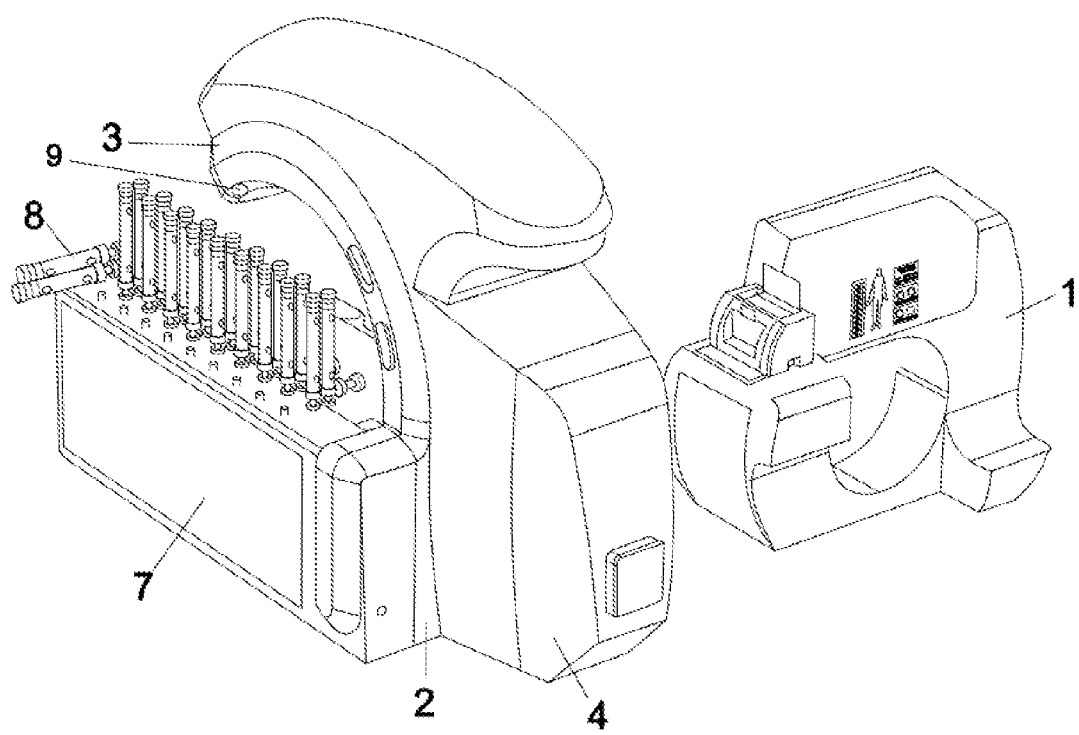
FIG. 2 is a second schematic diagram of a structure in accordance with the present disclosure.
1-main console, 2-physiotherapy couch, 3-mounting frame, 4-control box, 5-display screen, 6-control panel, 7-mounting box, 8-mechanical arm, 9-metal detector.

As shown in FIG. 1 and FIG. 2, a microwave physiotherapy acupoint acupuncture device includes a main console 1, and a physiotherapy couch 2. An end part of the physiotherapy couch 2 is provided with a mounting frame 3 and a control box 4. The mounting frame 3 is provided with a patient parameter display screen 5, a microwave source is arranged inside the control box 4, and a control panel 6 is provided outside the control box 4. A side part of the physiotherapy couch 2 is provided with a mounting box 7, a microwave magnetron is arranged inside the mounting box 7, and a mechanical arm 8 is arranged at a top of the mounting box 7. An end part of the mechanical arm 8 is provided with a microwave probe, and the microwave magnetron is connected to the microwave probe at the end part of the mechanical arm 8 through a line. The main console 1 is respectively connected to the display screen 5, the microwave source, the control panel 6, the microwave magnetron and the microwave probe through lines. The control panel 6 is respectively connected to the display screen 5, the microwave source, the microwave magnetron and the microwave probe through lines.

At least ten microwave magnetrons are arranged inside the mounting box 7, and at least ten mechanical arms are arranged at the top of the mounting box 7, and each microwave magnetron is correspondingly connected to the microwave probe on one of the mechanical arms 8 through a line. As required, the number of the microwave magnetrons and the mechanical arms 8 can be expanded to thirty, and the number of the microwave probes can be adjusted from one to thirty.

The mechanical arm 8 is a three joint mechanical arm or a universal bamboo pipe.

The mounting frame 3 is of a circular arc structure, and a metal detector 9 is arranged on a lower side face of a top of the mounting frame 3. The metal detector 9 is used for detecting whether a patient carries metals before microwave physiotherapy acupuncture, and the metal detector 9 may be used to detect whether the patient carries metal gadgets before physiotherapy.

The physiotherapy couch 2 is an electric physiotherapy couch.

A use method of a microwave physiotherapy acupoint acupuncture device includes the following steps:

(a) A power supply is switched on, and the whole acupoint acupuncture device is electrified, thus making the microwave physiotherapy acupoint acupuncture device in a standby state at the moment.

(b) A patient is settled on a physiotherapy couch 2, whether there are metals on and in the body of the patient is confirmed, the acupoints to be subjected to physiotherapy are confirmed, and positions of mechanical arms 8 are adjusted to align with the acupoints.

(c) Duration of physiotherapy is set, where the duration of physiotherapy is 0 to 30 minutes for a single session, preferably 15 minutes for a single session, and three sessions is a course of treatment.

(d) Microwave sources are turned on one by one through a main console 1 or a control panel 6, output power is adjusted to an acceptable range of the body of the patient, close attention should be paid to the reaction of the patient during physiotherapy, communication with the patient should be made for body feeling in time, and a stop button should be pressed immediately to cut off the microwave output instantly in case of an emergency.

(e) If the patient has no adverse reaction, the control panel 6 makes a prompt tone five seconds before the end of physiotherapy, then microwave output is stopped, and the main console 1 can print physiotherapy parameters.

(f) The mechanical arms 8 are removed from the body of the patient, the patient is slowly settled in a rest area to rest for 10 minutes, and after the observation period, the patient is free to move if no abnormal reaction exists.

A microwave connection port should be checked and screwed before physiotherapy, and a microwave probe interface should be checked again after physiotherapy, so as to ensure the firmness and reliability of the interface.

The microwave probes cannot be directly opposed to each other.

By adopting the above technical solution, the present disclosure has the beneficial effects that:

Compared with the existing microwave acupuncture equipment, an integrated microwave physiotherapy acupoint acupuncture device structure is employed, when a patient lies on a physiotherapy couch 2, ten acupoints of the patient can be subjected to microwave physiotherapy at the same time, and a lying posture of the patient can be adjusted through the electric physiotherapy couch 2, thus further improving the effect of microwave physiotherapy. Ten existing microwave acupuncture devices are required to achieve the use effect of the acupoint acupuncture device of the present disclosure. Microwave treatment of diseases is mainly achieved through thermal and biological effects. When acting on body tissues, the microwave may cause high-frequency oscillation of ions, water molecules and dipoles in tissue cells. When the microwave is low in output energy and less in radiant heat energy, local blood circulation can be increased, local metabolism can be accelerated, and local immunity can be enhanced. Therefore, the device can effectively improve local blood circulation, promote edema absorption, diminish inflammation, and relieve pain. According to the concept of traditional Chinese medicine, treatment with the microwave acupoint acupuncture device is safe and effective, with no irreversible toxic and side effects, no operation, convenient operation and no pain for patients.

In conclusion, a microwave physiotherapy acupoint acupuncture device and a use method thereof are provided. Compared with the existing microwave acupuncture equipment, an integrated microwave physiotherapy acupoint acupuncture device structure is employed, when a patient lies on a physiotherapy couch 2, ten acupoints of the patient can be subjected to microwave physiotherapy at the same time, and a lying posture of the patient can be adjusted through the electric physiotherapy couch 2, thus further improving the effect of microwave physiotherapy.

Compared with the existing microwave physiotherapy acupoint moxibustion instrument, an operator no longer needs to hold a probe for acupuncture operation, and when multiple acupoints of a patient need to be acupunctured at the same time, the microwave acupuncture physiotherapy can be carried out at multiple acupoints at the same time.

Finally, it should be noted that the above embodiments are only used to illustrate the technical solutions of the present disclosure rather than limiting the same. Although the present disclosure has been described in detail with reference to the foregoing embodiments, it should be understood by those of ordinary skill in the art that it is still possible to modify the technical solutions recorded in the foregoing embodiments, or to equivalently replace some or all of technical features; and that these modifications or replacements do not make the essence of the corresponding technical solutions deviate from the scope of the technical solutions of the embodiments of the present disclosure.

What is claimed is:

1. A microwave physiotherapy acupoint acupuncture device, comprising a main console, and a physiotherapy couch, wherein an end part of the physiotherapy couch is provided with a mounting frame and a control box, the mounting frame is provided with a patient parameter display screen, a microwave source is arranged inside the control box, and a control panel is arranged outside the control box; a side part of the physiotherapy couch is provided with a mounting box, a microwave magnetron is arranged inside the mounting box, and a mechanical arm is arranged at a top of the mounting box; an end part of the mechanical arm is provided with a microwave probe, and the microwave magnetron is connected to the microwave probe at the end part of the mechanical arm through one or more microwave probe lines; the main console is respectively connected to the display screen, the microwave source, the control panel, the microwave magnetron, and the microwave probe through a plurality of main console lines; the control panel is respectively connected to the display screen, the microwave source, the microwave magnetron, and the microwave probe through a plurality of control panel lines.

2. The microwave physiotherapy acupoint acupuncture device according to claim 1, wherein at least ten microwave magnetrons are arranged inside the mounting box, and at least ten mechanical arms are arranged at the top of the mounting box, and each microwave magnetron is correspondingly connected to the microwave probe on one of mechanical arms through a microwave probe line.

3. The microwave physiotherapy acupoint acupuncture device according to claim 2, wherein the mechanical arm is a three joint mechanical arm or a universal bamboo pipe.

4. The microwave physiotherapy acupoint acupuncture device according to claim 3, wherein the mounting frame is of a circular arc structure, and a metal detector is arranged at a lower side face of a top of the mounting frame.

5. The microwave physiotherapy acupoint acupuncture device according to claim 4, wherein the physiotherapy couch is an electric physiotherapy couch.

6. A use method of a microwave physiotherapy acupoint acupuncture device, comprising the following steps:
(a) turning on a power supply and electrifying the whole acupoint acupuncture device, thus making the microwave physiotherapy acupoint acupuncture device in a standby state at the moment;
(b) settling a patient on a physiotherapy couch, confirming that no metal is on and in the body of the patient, confirming acupoints to be subjected to physiotherapy, and adjusting positions of mechanical arms to align with the acupoints;
(c) setting duration of physiotherapy, wherein the duration of physiotherapy is 0 to 30 minutes for a single session, preferably 15 minutes for a single session, and three sessions for a course of treatment;
(d) turning on microwave sources one by one through a main console or a control panel, adjusting output power to an acceptable range of the body of the patient, paying close attention to reaction of the patient during physiotherapy, communicating with the patient for body feeling in time, and pressing a stop button immediately to cut off the microwave output instantly in case of an emergency;
(e) if the patient has no adverse reaction, sending, by the control panel, a prompt tone five seconds before the end of physiotherapy, then stopping microwave output, and printing, by the main console, physiotherapy parameters; and (f) removing the mechanical arms from the body of the patient, slowly settling the patient in a rest area to rest for 10 minutes, wherein after an observation period, the patient is free to move if no abnormal reaction exists.

7. The use method of a microwave physiotherapy acupoint acupuncture device according to claim 6, wherein a microwave connection port is checked and screwed before physiotherapy, and an interface of microwave probes are checked again after physiotherapy, so as to ensure the firmness and reliability of the interface.

8. The use method of a microwave physiotherapy acupoint acupuncture device according to claim 7, wherein the microwave probes are unable to be opposed to each other.

* * * * *